(12) United States Patent  
Kiester (10) Patent No.: US 8,006,578 B2  
(45) Date of Patent: Aug. 30, 2011

(54) APPARATUS AND METHOD FOR A HIGH SPEED ROTATION-TO-ROTATION OSCILLATION CONVERTER FOR SURGICAL USE

(76) Inventor: Douglas P. Kiester, Irvine, CA (US)

( * ) Notice: Subject to any disclaimer, the term of this patent is extended or adjusted under 35 U.S.C. 154(b) by 769 days.

(21) Appl. No.: 12/089,602

(22) PCT Filed: Sep. 29, 2006

(86) PCT No.: PCT/US2006/038146  
§ 371 (c)(1), (2), (4) Date: Apr. 11, 2008

(87) PCT Pub. No.: WO2007/047070  
PCT Pub. Date: Apr. 26, 2007

(65) Prior Publication Data  
US 2008/0234716 A1    Sep. 25, 2008

Related U.S. Application Data

(60) Provisional application No. 60/726,252, filed on Oct. 12, 2005.

(51) Int. Cl.  
*F16H 37/16* (2006.01)

(52) U.S. Cl. .......................................................... 74/23  
(58) Field of Classification Search ............... 74/20, 21, 74/22 A, 22 R, 23, 24, 25, 26, 27; 606/1, 606/79, 85, 167–171, 180, 82, 84, 174  
See application file for complete search history.

(56) References Cited

U.S. PATENT DOCUMENTS  
4,807,452 A * 2/1989 Brenner ........................ 68/23.3  
* cited by examiner

*Primary Examiner* — Thomas R Hannon  
*Assistant Examiner* — Phillip A Johnson  
(74) *Attorney, Agent, or Firm* — Daniel L. Dawes; Marcus C. Dawes (57) ABSTRACT

A converter for use in a high speed rotationally oscillating surgical burring device comprises an output shaft, and a rotationally oscillating secondary drive rotor coupled to the output shaft. The secondary drive rotor is arranged and configured with a size and mass to minimize its angular momentum. A unidirectionally rotating primary drive rotor is provided. A linearly reciprocating transmission converts unidirectional rotation to bidirectional rotational oscillation coupling the primary and secondary drive rotors. The transmission is arranged and configured with a size and mass to minimize its linear momentum. An input shaft is coupled to the rotating primary drive rotor to which a unidirectional rotational force is applied.

10 Claims, 13 Drawing Sheets

APPARATUS AND METHOD FOR A HIGH SPEED ROTATION-TO-ROTATION OSCILLATION CONVERTER FOR SURGICAL USE

RELATED APPLICATIONS

The present application is related to U.S. Provisional Patent Application, Ser. No. 60/726,252, filed on Oct. 12, 2005, which is incorporated herein by reference and to which priority is claimed pursuant to 35 USC 119.

BACKGROUND OF THE INVENTION

1. Field of the Invention

The invention relates to the field of rotationally oscillating burr for surgical use.

2. Description of the Prior Art

The need and desirability for a rotationally oscillating burr for surgical use is well known. Indeed, it is this desire to have a device which cuts away hard tissues while leaving soft tissues unharmed, that was the initial driving force which led to the multiple ultrasonic cutting instruments which have been developed.

The application to which the invention is directed is spine surgery, especially the decompression of the spinal canal, where the removal of bone in the presence of soft nervous structures is routine. Standard burrs can wrap up a nerve root in milliseconds, which is a disaster. As such, the final few millimeters of decompression are often very labor intensive and tedious for the surgeon.

BRIEF SUMMARY OF THE INVENTION

The illustrated embodiment of the invention is a rotational oscillating device which successfully satisfies the following constraints:

It operates at very high speed (60,000 Hz and above).
It has very little vibration.
Any vibration which does occur is not in the side-to-side or front-to-back planes.
Its components are coaxial.
It is durable.
It does not damage itself at high speed.
For safety if damaged it does not fail by reverting to a full rotational mode of operation.
It is small for ease of use.
For safety if operates in both forward and reverse.

Because the illustrated embodiment will not wrap up a nerve and won't cut the dura, unless it is sandwiched between the burr and a hard surface, the final stages of spinal decompression can be done with far greater safety and efficiency than had been achievable with any prior art surgical instrument. Thus, it must also be clearly understood that the invention has multiple other anatomic surgical applications other than spinal decompression or spinal surgery.

Because the tool driven by the illustrated embodiment stops, rotates, stops and changes direction and then rotates again many times per second, it is very important that the it have as little angular momentum a possible. This makes an oscillating motor less desirable than a rotation-to-rotation oscillation converter. The illustrated embodiment is a rotation-to-rotation oscillation converter, the parts of which that actually oscillate are given a very small diameter or mass to minimize their angular momentum. The only parts which vibrate are also very small, and therefore very light to again provide low angular momentum. The moving parts are a drive pin and pin caps. The drive pin and pin caps move up and down along the long axis of the device. As such the vibration is directly into and out of the drive motor, which therefore uses the drive motor as a vibration damper. Because any vibration is into and out of the wound or surgical site, the burr remains very stable during use.

More particularly, the illustrated embodiment is a converter for use in a high speed rotationally oscillating surgical burring device comprising an output shaft, and a rotationally oscillating secondary drive rotor coupled to the output shaft. The secondary drive rotor is arranged and configured with a size and mass to minimize its angular momentum. A unidirectionally rotating primary drive rotor is provided. A linearly reciprocating transmission converts unidirectional rotation to bidirectional rotational oscillation coupling the primary and secondary drive rotors. The transmission is arranged and configured with a size and mass to minimize its linear momentum. An input shaft is coupled to the rotating primary drive rotor to which a unidirectional rotational force is applied.

The transmission has its minimized linear momentum aligned with the longitudinal axis of rotation of the output shaft and preferably is only along the longitudinal axis of rotation of the output shaft.

The output shaft, the secondary drive rotor, the primary drive rotor, the transmission and the input shaft are operable in both forward and reverse senses.

The converter further comprising a means for preventing full rotation of the secondary drive rotor in event of failure. The converter comprises a safety piece to disengage the secondary rotor from the primary rotor in the event of malfunction causing full rotation of the secondary rotor with the primary rotor.

The output shaft, the secondary drive rotor, the primary drive rotor, the transmission and the input shaft each have a degree of azimuthal symmetry and are each mutually coaxial with each other.

The output shaft, the secondary drive rotor, the primary drive rotor, the transmission and the input shaft has the ability to operate at a speed so that the output shaft oscillates at 60 kHz or greater. It is to be understood that the invention also contemplates a variable speed operation at speeds lower than 60 kHz oscillation.

In the illustrated embodiment the secondary drive rotor has a spiral slot defined therethrough. The transmission comprises a drive pin disposed through the spiral slot, so that the secondary drive rotor rotationally oscillates as the drive pin longitudinally reciprocates. A stationary guide has a linear slot defined therethrough through which the drive pin is disposed to maintain the drive pin in a fixed plane of oscillatory linear motion. A cam follower or a pair of cam followers are coupled to the drive pin, where the primary drive rotor has a cylindrical bore in which an elliptical groove is defined. The cam follower engages the elliptical groove so that the drive pin is longitudinally reciprocated within the primary drive rotor as the primary drive rotor unidirectionally rotates.

In the preferred embodiment the drive pin has two opposing ends and the transmission further comprises a pair of cam followers. One cam follower is coupled to each end of the drive pin. A pair of elliptical intersecting grooves are defined in the cylindrical bore. Each cam follower engages one of the pair of elliptical grooves so that the drive pin is longitudinally reciprocated within the primary drive rotor as the primary drive rotor unidirectionally rotates.

The elliptical groove and spiral slot are arranged and configured in the primary and secondary rotors respectively to provide a minimal linear velocity of the drive pin when the drive pin is near or at the ends of the spiral groove in the secondary rotor.

The invention is also a method of providing oscillating rotational motion to surgical burring device comprising the steps of unidirectionally rotating an input shaft, unidirectionally rotating a primary drive rotor by the input shaft, transforming the unidirectional rotation of the primary drive rotor into linearly reciprocating motion of a reciprocating component which is arranged and configured with a size and mass to minimize its linear momentum, transforming the linearly reciprocating motion of the reciprocating component into bidirectional rotational oscillation of a secondary drive rotor, which is arranged and configured with a size and mass to minimize its angular momentum, and rotationally oscillating an output shaft coupled to the secondary drive rotor.

The step of transforming the unidirectional rotation of the primary drive rotor into linearly reciprocating motion of a reciprocating component comprises generating linearly reciprocating motion of a reciprocating component along a direction of the longitudinal axis of rotation of the output shaft. The step of generating linearly reciprocating motion of a reciprocating component along a direction of the longitudinal axis of rotation of the output shaft comprises generating linearly reciprocating motion only along the longitudinal axis of rotation of the output shaft.

The steps of rotating the input shaft, rotating the primary drive rotor, transforming the unidirectional rotation of the primary drive rotor into linearly reciprocating motion of a reciprocating component, transforming the linearly reciprocating motion of the reciprocating component into bidirectional rotational oscillation of the secondary drive rotor, and rotationally oscillating the output shaft are performed or performable in both forward and reverse senses.

The method further comprises the step of preventing full rotation of the secondary drive rotor in event of failure.

The steps of rotating the input shaft, rotating the primary drive rotor, linearly reciprocating the reciprocating component, bidirectional rotational oscillating the secondary drive rotor, and rotationally oscillating the output shaft comprises performing each motion mutually coaxially with each other.

The steps of rotating the input shaft, rotating the primary drive rotor, transforming the unidirectional rotation of the primary drive rotor into linearly reciprocating motion of a reciprocating component, transforming the linearly reciprocating motion of the reciprocating component into bidirectional rotational oscillation of the secondary drive rotor, and rotationally oscillating the output shaft are each performed at a speed so that the output shaft oscillates at 60 kHz or greater.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 to be accorded full statutory equivalents under 35 USC 112. The invention can be better visualized by turning now to the following drawings wherein like elements are referenced by like numerals.

BRIEF DESCRIPTION OF THE DRAWINGS

FIGS. 1a-1b are views of the primary drive rotor of the converter.

FIG. 1b is a longitudinal horizontal cross sectional view taken through section 1b-1b of FIG. 1a.

FIG. 1c is a longitudinal vertical cross sectional view taken through section 1c-1c of FIG. 1a.

FIG. 1d is a perpendicular cross sectional view taken through section 1d-1d of FIG. 1a.

FIGS. 3a-3d are views of the secondary drive rotor.

FIGS. 4a-4d are view of the distal guide.

FIGS. 5a-5d are views of the proximal cover.

FIGS. 6a-6c are assembly views of the converter.

FIGS. 7a-7c are views of a first method of assembly of the converter.

FIGS. 8a-8d are views of a second method of assembly of the converter.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

This illustrated embodiment of the invention takes a rotational movement and converts it into rotational oscillation. The converter 10 shown in assembled view in FIG. 6*c* is comprised of five basic components as illustrated in exploded view in FIGS. 6*a* and 6*b*: a primary drive rotor 12 which is an input single direction rotational drive; a secondary oscillating output drive 14, a drive pin 16 and drive pin end caps 18, a fixed or immobile deep guide and distal cover 20, and a proximal cover 22.

Figure 6A:
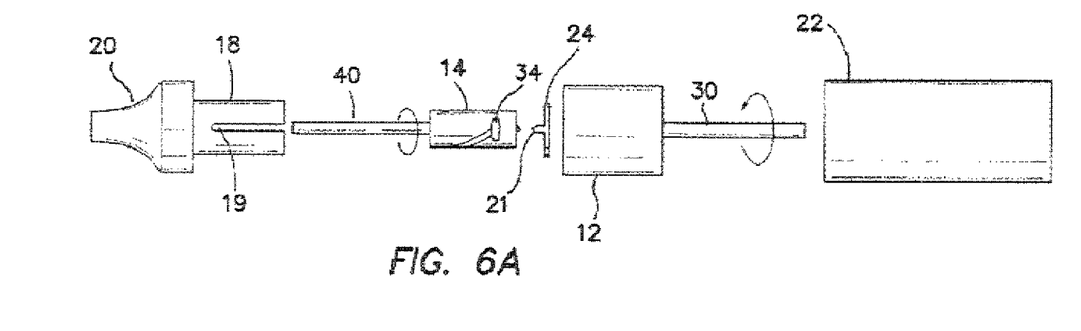
FIG. 6a is an exploded assembly side elevational view of the converter.
Figure 6B:
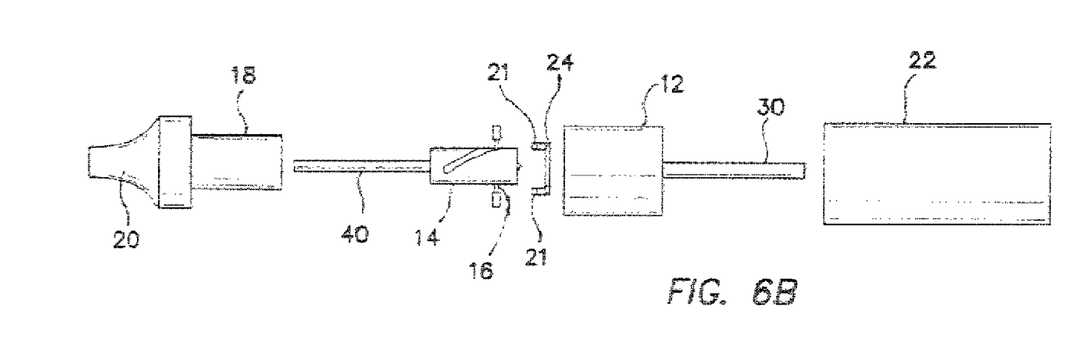
FIG. 6b is an exploded assembly top elevational view of the converter.
Figure 6C:
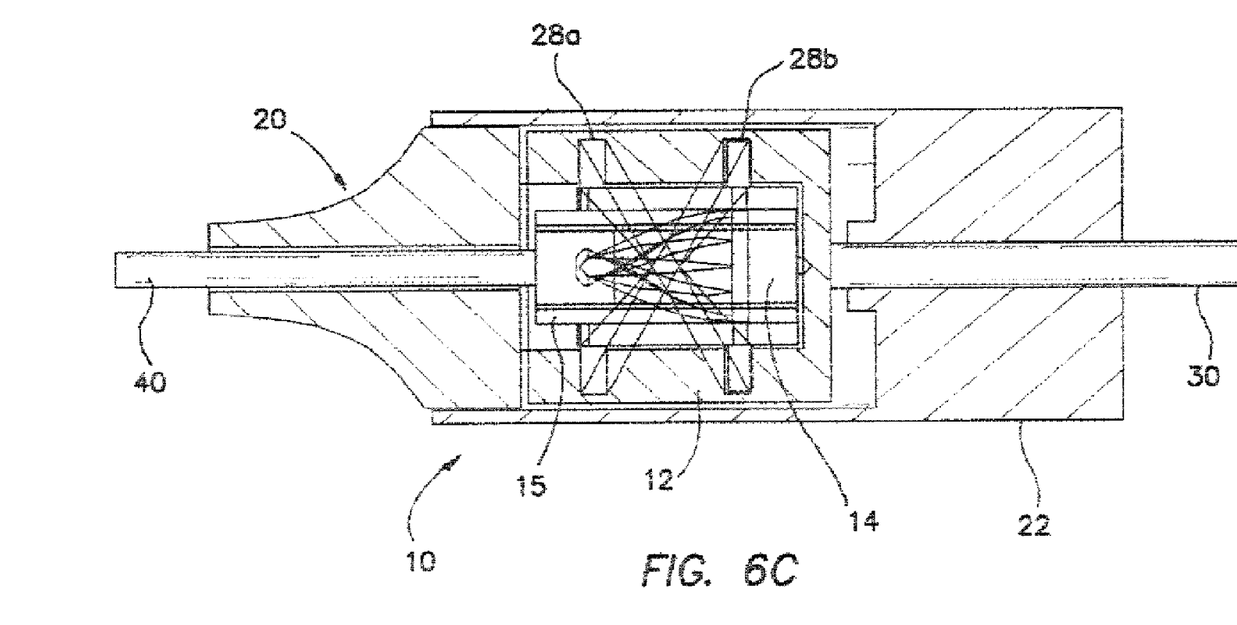
FIG. 6c is an assembled view of the converter.

An optional deep insulating safety piece 24 shown in FIGS. 6A and 6B further isolates the rotating drive 12 from the oscillating drive 14 especially in the event of a failure. The safety piece 24 mounts to the fixed deep guide and distal cover 20 described above.

Turn and consider first the primary rotor as shown in FIGS. 1*a*-1*d*. As shown in the perspective view of FIG. 1*a* the primary rotor 12 is comprised of a tube 26 with a cylindrical bore 27 with a pair of intersecting elliptical grooves 28*a* and 28*b* cut into bore 27 inside of the tube 26 as seen in the side cross sectional view of FIG. 1*c* and mid perpendicular end cross sectional view of FIG. 1*d*. The elliptical grooves 28*a* and 28*b* are cut so that at all points within the elliptical grooves 28*a* and 28*b*, one elliptical groove 28*a* or 28*b* is exactly diametrically positioned opposite the other elliptical groove 28*b* or 28*a* of the pair respectively. As best seen in the longitudinal cross sectional view of FIG. 1*b* one end 29 of the tube 26 is open, and the other end 31 is connected to a drive shaft 30 in order to input a rotational force or drive into the converter 10 from an electrical motor (not shown).

Figure 1A:
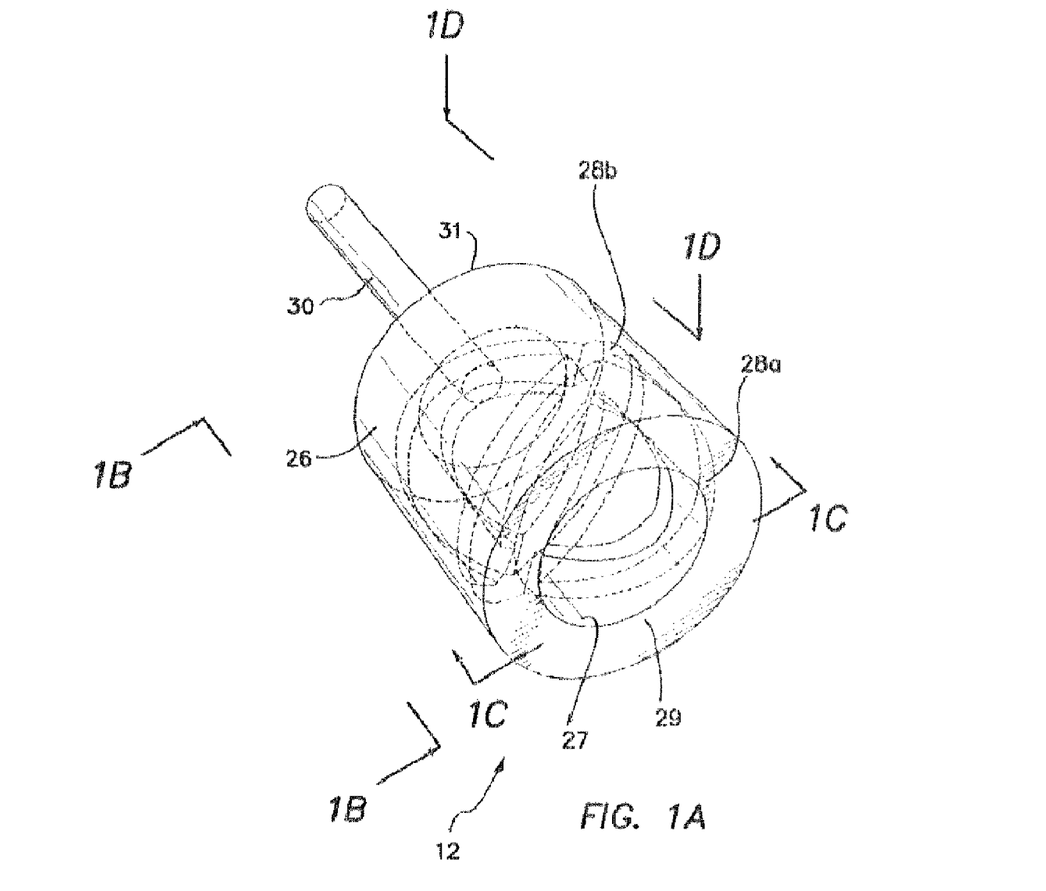
FIG. 1a is perspective view illustrated in phantom outline a pair of elliptical intersecting grooves defined into the cylindrical bore defined in the primary drive rotor.
Figures 1B, 1D:
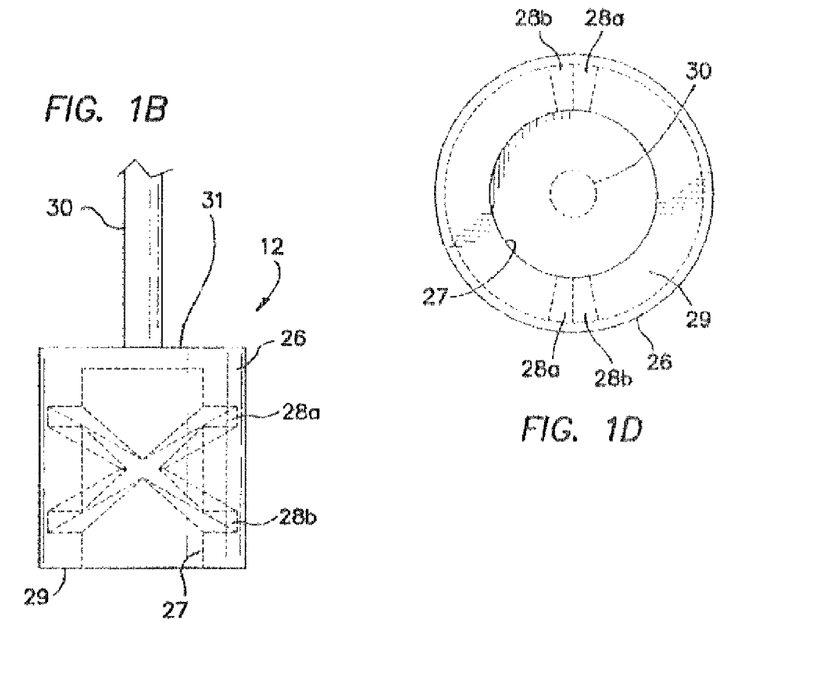
Figure 1C:
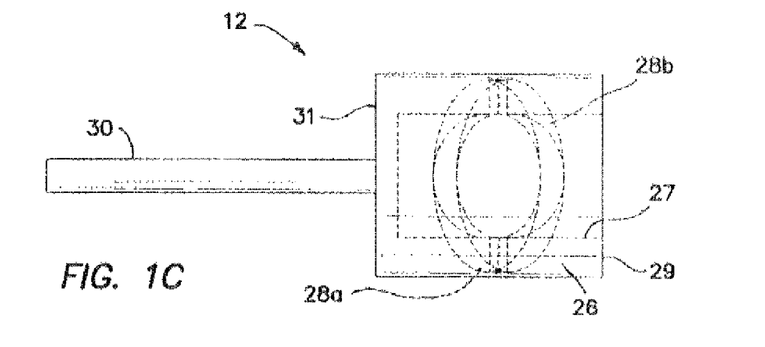
Figure 2:
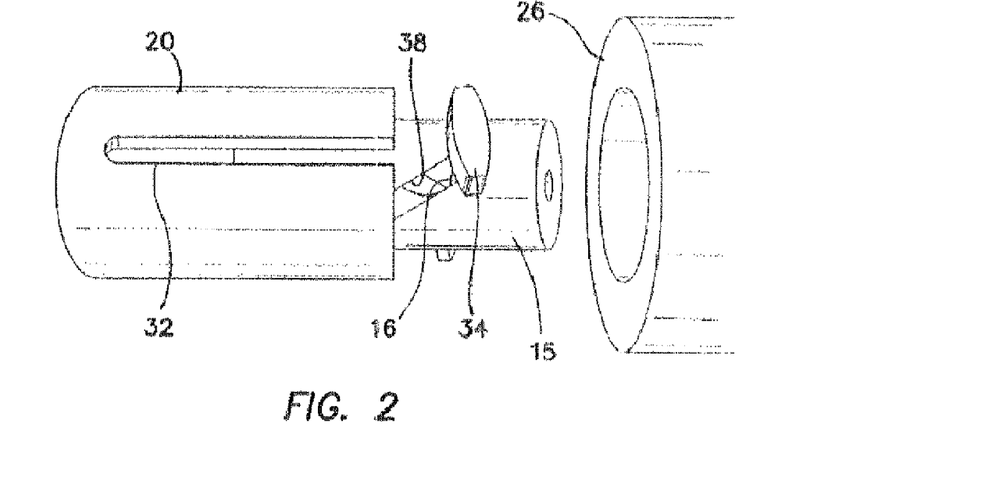
FIG. 2 is an exploded perspective view of a portion of the primary drive rotor, secondary drive rotor and a portion of the distal guide of the converter.

As the tube 26 rotates, a pair of cam followers 34 connected one to each end of a drive pin 16 as best seen in the perspective view of FIG. 2 is disposed in the grooves 28*a* and 28*b* and follows a reciprocating longitudinal path along the axis of tube 26 as it rotates.

Turn now and consider the drive pin 16 in oscillating drive 14 in greater detail as shown in the exploded perspective view of FIG. 2. The drive pin 16 is maintained in fixed angular orientation in space by a fixed deep cylindrical guide 20 while being allowed to reciprocate longitudinally by being captured within a fixed longitudinal slot 32 in the fixed deep guide 20. Drive pin 16 is not allowed to rotate. Each end of the pin 16 is provided with a cam follower head 34 which is retained or disposed in one of the elliptical grooves 28*a* or 28*b* at all times as described above. As the tube 26 of primary drive 12 rotates, the drive pin 16 follows the grooves 28*a* or 28*b* in the tube 26, and reciprocates along the longitudinal axis of the device 10 as defined by slot 32 without rotation.

The tapering of cam follower heads 34 serve to prevent the ends of the drive pin 16 from jumping into the wrong groove 28*a* or 28*b* where the grooves 28*a* and 28*b* cross or intersect, and to decrease wear on the pin 16. The tapered cam follower heads 34 are shaped on their inner radial surface 35 as shown in FIG. 3*d* so that they also act as a cylindrical segmental bushing against the outside cylindrical surface of fixed deep guide 20 as the inner radial surface of head 34 slides on the outside surface of guide 20.

Figure 3A:
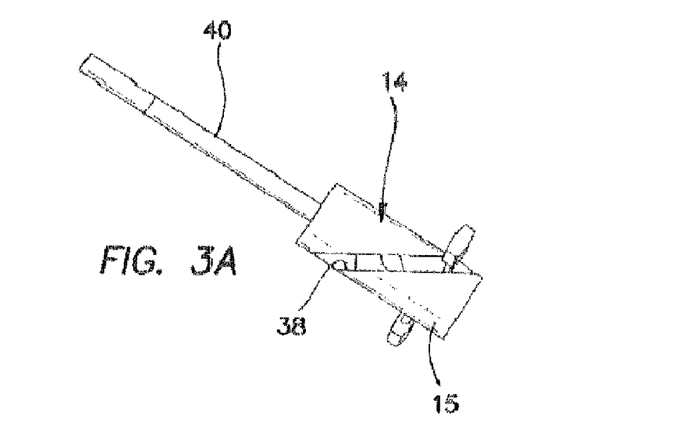
FIG. 3a is a perspective view of the secondary drive rotor and output shaft of the converter.
Figures 3B, 3D:
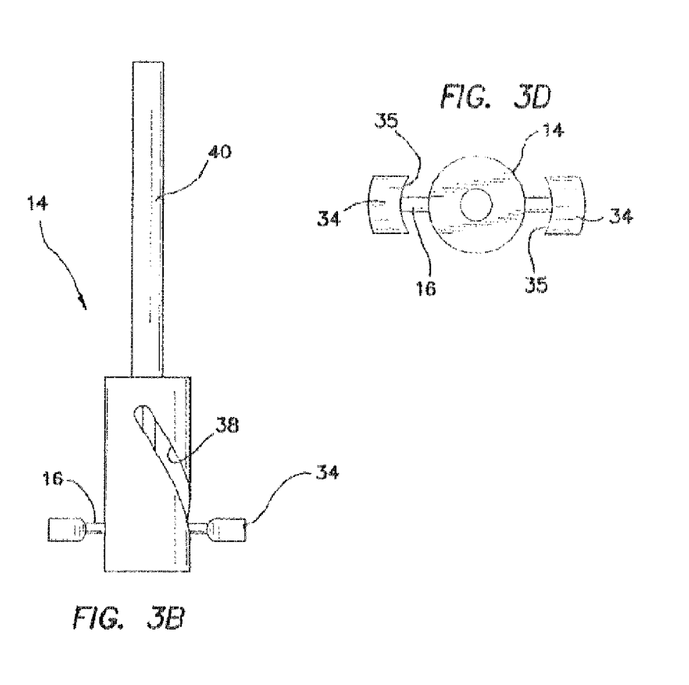
FIG. 3b is a top plan elevational view of the secondary drive rotor and output shaft of the converter.
FIG. 3d is an end plan elevational view of the secondary drive rotor and output shaft of the converter.
Figure 3C:
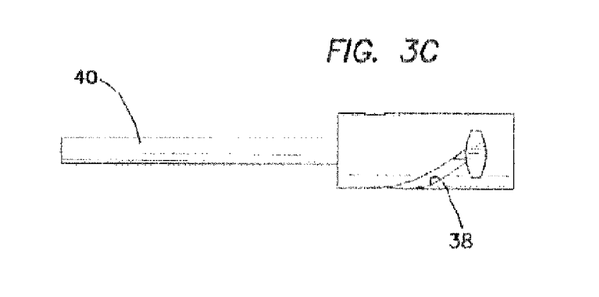
FIG. 3c is a side plan elevational view of the secondary drive rotor and output shaft of the converter.

Thus it can now be appreciated that oscillating output drive 14 as shown in rotated perspective view in FIG. 3*a*, in side elevational view in FIG. 3*b*, and a 90° rotated side elevational view in FIG. 3*c* comprises an oscillating drive cylinder 15 in combination with drive pin 16 and cam follower heads 34. FIG. 3*d* shows an end elevational view of drive 14 and better illustrates the shape of the cam heads 34 and the shaped inner radial surface 35. The oscillating drive cylinder 15 has an oblique spiral slot 38 cut through its diameter. Drive pin 16 is disposed through spiral slot 38 and thus engages drive cylinder 15. As the drive pin 16 is forced to reciprocate along the device 10's longitudinal axis, the oscillating drive cylinder 15 is forced to rotate, first in one direction, then in the opposite direction according to the degree of the spiral rotation defined by slot 38 in drive cylinder 15. Oscillation of drive cylinder 15 in turn oscillates the output shaft 40 through the same oscillating angular segment.

Because the grooves 28*a* and 28*b* in the primary rotor 12 which push the drive pin 16 are elliptical, the device 10 naturally slows the oscillating rotation of the oscillating drive 14 before each rotational direction change, i.e. the position of the slowest rate at which cam follower head 34 is driven in grooves 28*a* and 28*b* is arranged and configured by the positioning of the eccentricity of the elliptical shape in tube 26 to be aligned at or near the end points of oscillation of pin 16 in spiral slot 38 defined in drive 14.

Figure 4A:
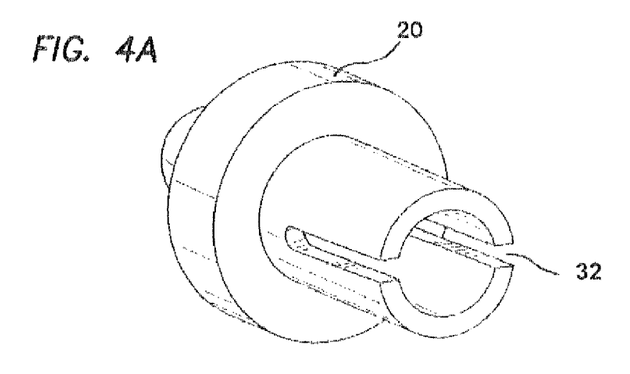
FIG. 4a is a perspective view of the distal guide of the converter.
Figure 4B:
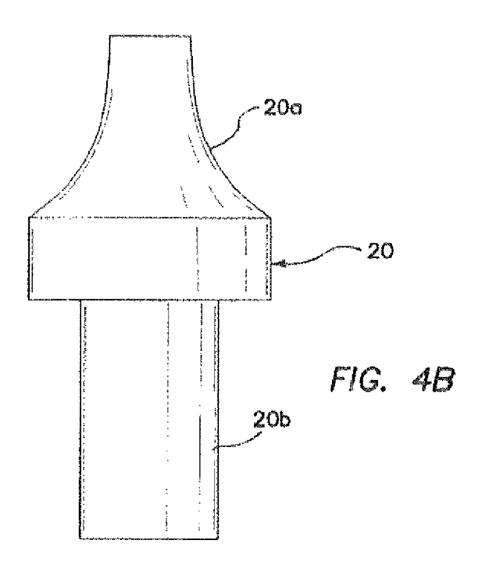
FIG. 4b is a top plan elevational view of the distal guide of the converter.
Figure 4C:
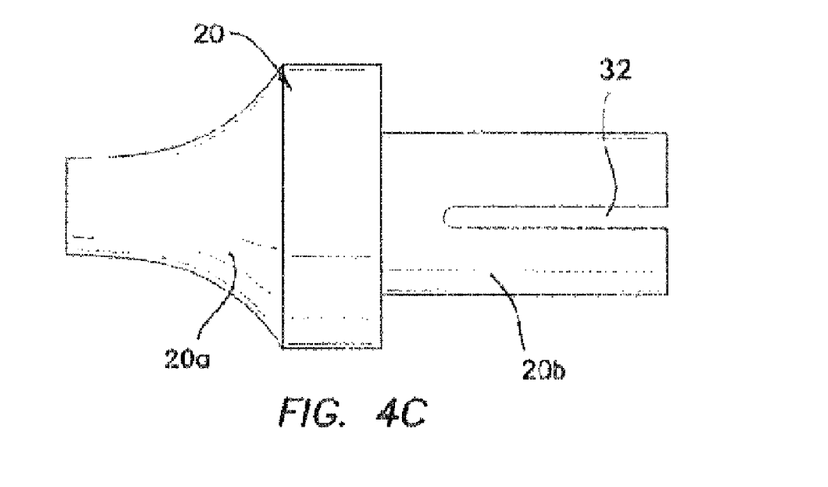
FIG. 4c is a side plan elevational view of the distal guide of the converter.
Figure 4D:
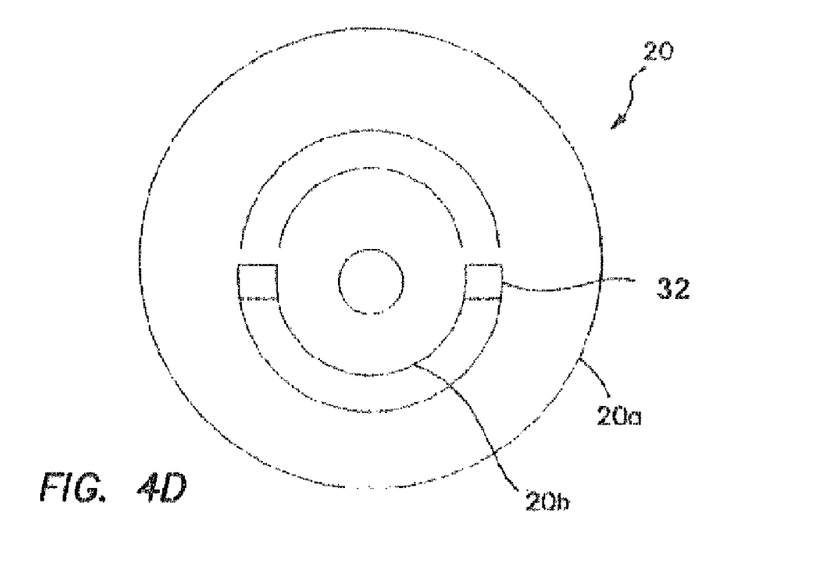
FIG. 4d is an end plan elevational view of the distal guide of the converter.
Figure 5A:
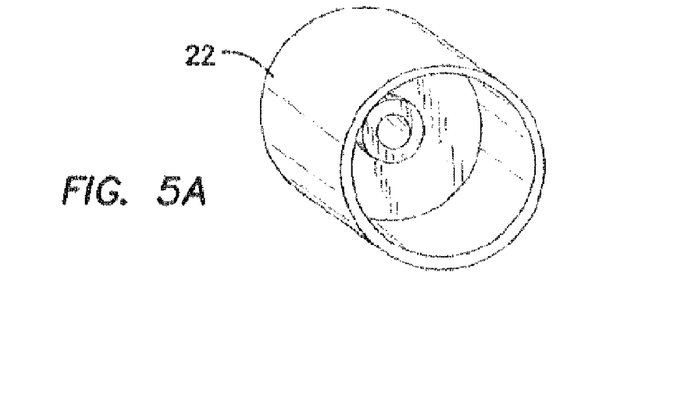
FIG. 5a is a perspective view of the proximal cover of the converter.
Figure 5B:
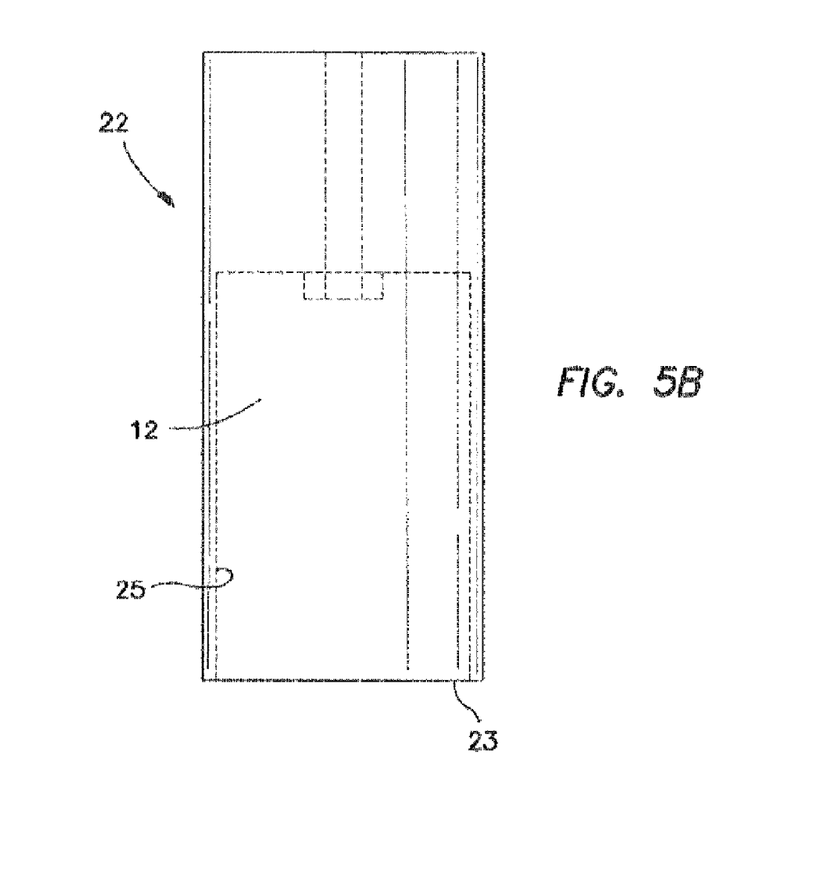
FIG. 5b is a top plan view of the proximal cover of the converter with the primary drive rotor shown in phantom outline therein.
Figure 5C:
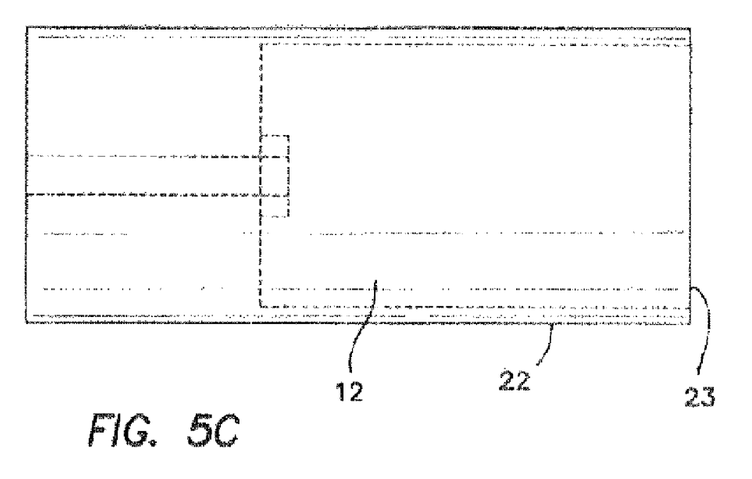
FIG. 5c is a side plan view of the proximal cover of the converter with the primary drive rotor shown in phantom outline therein.
Figure 5D:
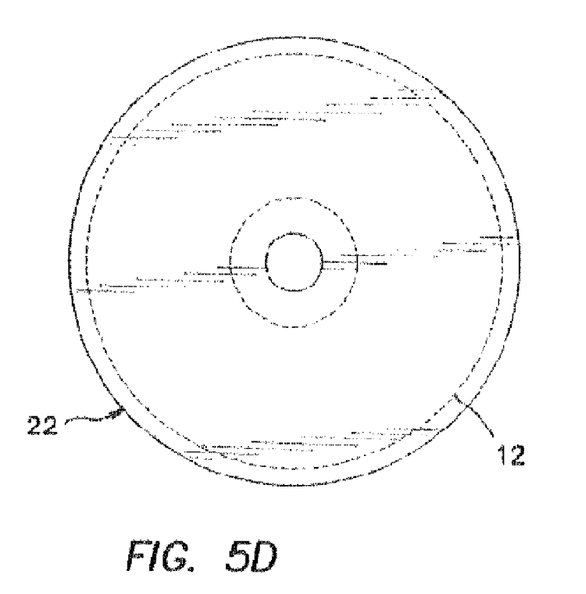
FIG. 5d is an end plan view of the proximal cover of the converter with the primary drive rotor shown in phantom outline therein.

Turn now and consider in greater detail the fixed deep guide and distal cover 20, which has an integral distal cover portion 20*a* and proximal slotted shaft portion 20*b* as shown in FIGS. 4*b*-4*c*. The portion 20*b* as illustrated in the proximal end perspective view of FIG. 4*a* prevents rotation of the guide pin 16 by means of slot 38, acts as part of the bushings or a mount for the rotational bushings of the oscillating drive 14, and acts as a distal cover for the distal end of the converter 10. Guide portion 20*a* is firmly fixed to a proximal cover 22 shown in FIGS. 6*a*-6*c* so that guide 20 cannot rotate. The drive pin 16 reciprocates or slides longitudinally up and down the longitudinal slot 32 cut in the deep guide portion 20*b*. In other words, the outer case of the apparatus comprised of distal cover 20 and proximal cover 22 are firmly attached or coupled to a motor housing (not shown) held or controlled by the surgeon so that longitudinal slot 32 is similarly prevented from rotating, thereby insuring that pin 16 is restrained to oscillate linearly.

Turn now and consider in greater detail the proximal cover 22 as shown in FIGS. 5*a*-5*d*. The proximal cover 22 mounts firmly to a motor housing (not shown) so that it cannot rotate. Proximal cover 22 also attaches at its end 23 to the deep guide 20 so that guide 20 too cannot rotate. Cover 22 also provides bushing support or provides the bushings 25 for the primary rotor 12. Cover 22 is sealed so that converter 10 can hold or be at least partially filled with a lubricant.

In one embodiment of the invention an optional deep insulating safety piece 24 is included as shown in FIGS. 6*a* and 6*b*. The safety piece 24 is placed between the primary rotor 12 and oscillating rotor 14, and is locked to the deep guide 20.

Safety piece 24 takes the form of a circular washer with two longitudinally projecting, diametrically opposite prongs 21 which fit into groove 38 of guide 20. Safety piece 24 is fixed to stationary proximal cover 22 by adhesive or other conventional means and normally, pin 16 will oscillate longitudinally between the two opposing prongs 21 and the distal end 19 of slot 38. Since the primary rotor 12 and oscillating cylinder 15 are coupled through pin 16, if pin 16 becomes jammed in groove 28a or 28b, oscillating cylinder 15 potentially can begin to unidirectionally rotate in the case of a jam with primary rotor 12 instead of oscillating. With safety piece 24 in place, full rotation of the oscillating cylinder 15 is impossible without jamming against, stressing or breaking the deep guide 20. In a properly designed unit, the drive pin 16 is designed to break first. The completely assembled converter 10 is shown in cut-away side cross sectional view in FIG. 6c without the inclusion of safety piece 24.

Figure 7A:
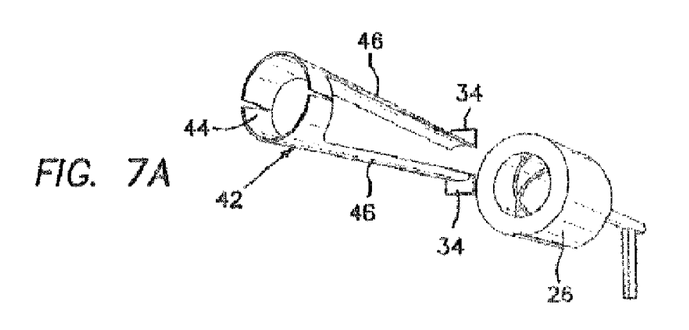
FIG. 7a is a perspective view in a first step of a first embodiment of a process of assembly of the converter where the cams are being inserted into the primary drive rotor.
Figures 7B, 7C:
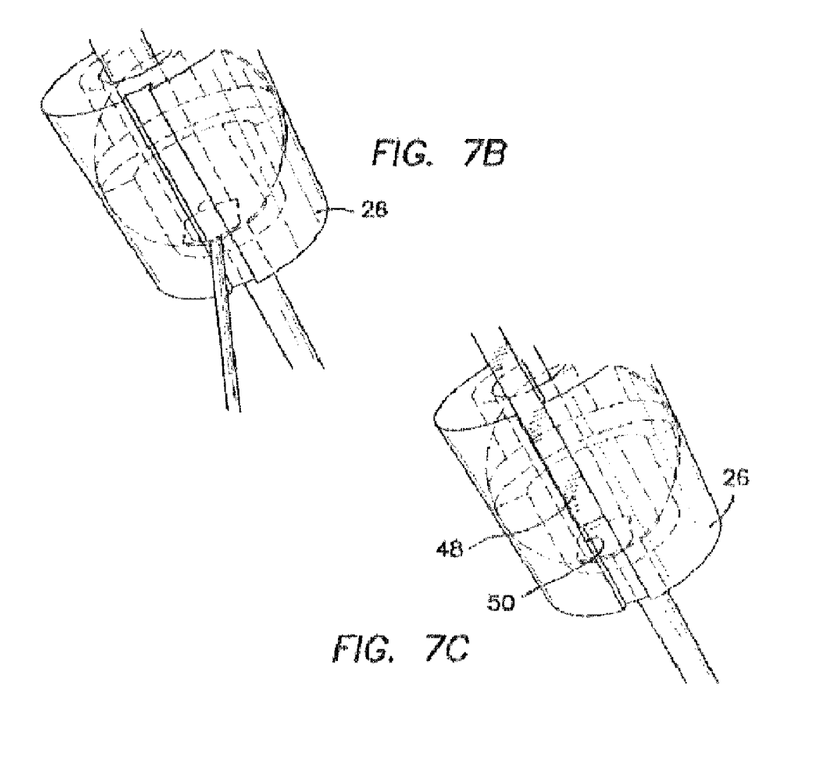
FIG. 7b is a perspective view in a second step of the first embodiment of a process of assembly of the converter where the drive pin is being inserted into the primary drive rotor.
FIG. 7c is a perspective view in a third step of the first embodiment of a process of assembly of the converter where the drive pin is being locked into place.

Consider now two assembly procedures used for fabricating converter 10. A first assembly process is shown in FIGS. 7a-7c. In FIG. 7a a jig 42 is used to insert the follower cam heads 34 into grooves 28a and 28b into tube 26 within bore 27. Jig 42 has a cylindrical proximal end 44 from which two diametrically opposing, resilient arms 46, the distal ends of which carry cam heads 34. Pin 16 is then inserted through aligned holes defined in tube 26, through slot 38 in driver cylinder 15 and into both cam follower heads 34 as shown in FIG. 7b. A retaining bar 48 is then slid into a slot 50 defined in outside of tube 26 to retain pin 26 in position as shown in FIG. 7c.

Figure 8A:
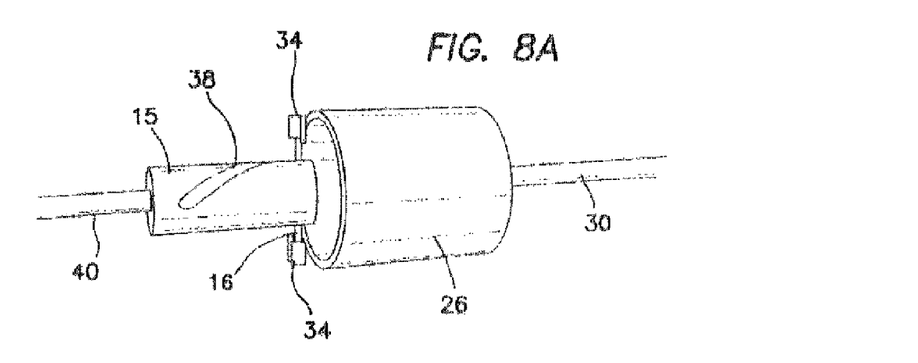
FIG. 8a is a perspective view in a first step of a second embodiment of a process of assembly of the converter where a subassembled secondary drive rotor is being inserted into the primary drive rotor.
Figure 8B:
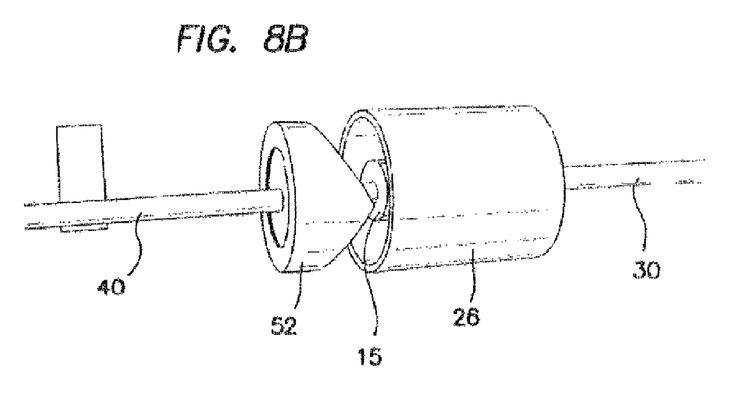
FIG. 8*b* is a perspective view in a second step of a second embodiment of a process of assembly of the converter where a bushing is being inserted into the primary drive rotor.
Figure 8C:
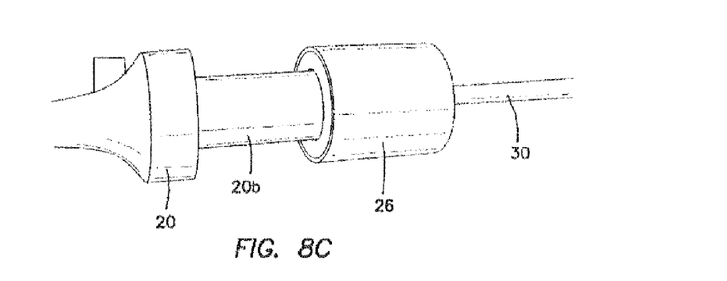
FIG. 8*c* is a perspective view in a third step of a second embodiment of a process of assembly of the converter where the guide is being inserted between the secondary drive rotor and primary drive rotor.
Figure 8D:
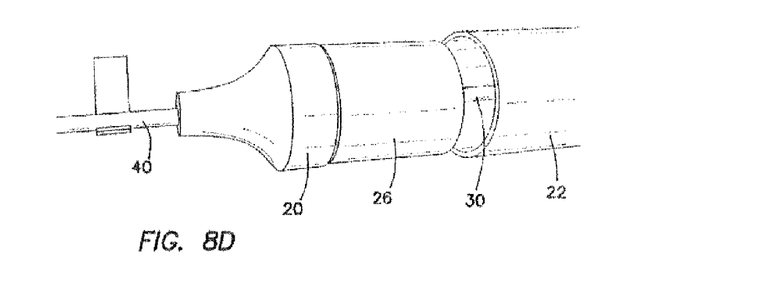
FIG. 8*d* is a perspective view in a fourth step of a second embodiment of a process of assembly of the converter where the proximal cover is being inserted over the primary drive rotor and affixed to the guide.

Another embodiment of an assembly process is illustrated by FIGS. 8a-8d. With pin 26 and cam follower heads 34 already being in position in rotor cylinder 15, subassembled rotor cylinder 15 with pin 16 and heads 34 is disposed into grooves 28a and 28b in tube 26 as shown in FIG. 8a. A bushing 52 is then inserted into tube 26 to center rotor cylinder 15 therein as shown in FIG. 8b. Guide 20 is then inserted into the bushing 52 between tube 26 and rotor cylinder 15 as shown in FIG. 8c. Proximal cover 22 is then inserted over tube 26 and placed into engagement with guide 20 as shown in FIG. 8d.

In summary, the conversion of high speed unidirectional rotational motion to rotational oscillation is best accomplished with a conversion transmission which considers momentum considerations. Using an oscillating motor results in very high angular momentum imparted to the driven tool, which is incompatible with high speed oscillation. With the design of the illustrated embodiment the oscillating parts are minimized to one component, namely cylinder 15, which is provided with a very small diameter and mass resulting in a minimal angular momentum.

Vibration and instability are caused by the linear momentum of component parts within the device. The only linear momentums generated within converter 10 are generated by the drive pin 16 and cam heads 34. Again drive pin 16 and cam heads 34 are small and thus have a low linear momentum. More importantly their momentum is coaxial with the center of rotation, perfectly balanced, and is coupled into the connected stationary driving motor, which has a comparatively larger mass. There is no momentum generated in any direction except along the operational or longitudinal axis of the converter 10. Because the little linear momentum which generated is coupled into and out of the driving motor, it is significantly dampened.

Because the device is coaxial, small, and cylindrical; it works very well as an add-on to existing surgical equipment. It does not significantly add to the size and weight of existing high-speed burr devices.

While this device is designed to cut away bone from the nervous elements of the spine, it clearly has other applications. Anywhere where hard structures need to be removed without damaging nearby or surrounding soft structures, converter 10 would be useful.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following invention and its various embodiments.

Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the invention is explicitly contemplated as within the scope of the invention.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

I claim:

1. A converter for use in a high speed rotationally oscillating surgical burring device comprising:
    an output shaft;
    a rotationally oscillating secondary drive rotor coupled to the output shaft, the secondary drive rotor being arranged and configured with a size and mass to minimize its angular momentum;
    a unidirectionally rotating primary drive rotor;
    a linearly reciprocating transmission for converting unidirectional rotation to bidirectional rotational oscillation coupling the primary and secondary drive rotors, the transmission being arranged and configured with a size and mass to minimize its linear momentum; and
    an input shaft coupled to the rotating primary drive rotor to which a unidirectional rotational force is applied,
    wherein the secondary drive rotor has a spiral slot defined therethrough, and where the transmission comprises:
        a drive pin disposed through the spiral slot, so that the secondary drive rotor rotationally oscillates as the drive pin longitudinally reciprocates;
        a stationary guide having a linear slot defined therethrough through which the drive pin is disposed to maintain the drive pin in a fixed plane of oscillatory linear motion; and
        a cam follower coupled to the drive pin where the primary drive rotor has a cylindrical bore in which an elliptical groove is defined, the cam follower engaging the elliptical groove so that the drive pin is longitudinally reciprocated within the primary drive rotor as the primary drive rotor unidirectionally rotates.

2. The converter of claim 1 where the output shaft has a longitudinal axis of rotation and where the transmission has its minimized linear momentum aligned with the longitudinal axis of rotation of the output shaft.

3. The converter of claim 2 where the transmission has its minimized linear momentum is only along the longitudinal axis of rotation of the output shaft.

4. The converter of claim 1 further comprising means for preventing full rotation of the secondary drive rotor in event of failure.

5. The converter of claim 1 where the output shaft, the secondary drive rotor, the primary drive rotor, the transmission and the input shaft each have a degree of azimuthal symmetry and are each mutually coaxial with each other.

6. The converter of claim 1 where the output shaft, the secondary drive rotor, the primary drive rotor, the transmission and the input shaft are arranged and configured to be capable of operating at a speed such that the output shaft oscillates at 60 kHz or greater.

7. The converter of claim 1 where the drive pin has two opposing ends and where the transmission further comprises a pair of cam followers, one cam follower coupled to each end of the drive pin, and where a pair of elliptical intersecting grooves are defined in the cylindrical bore, each cam follower engaging one of the pair of elliptical grooves so that the drive pin is longitudinally reciprocated within the primary drive rotor as the primary drive rotor unidirectionally rotates.

8. The converter of claim 1 where the elliptical groove and spiral slot are arranged and configured in the primary and secondary rotors respectively to provide a minimal linear velocity of the drive pin when the drive pin is near or at the ends of the spiral groove in the secondary rotor.

9. The converter of claim 1 further comprising a safety piece to disengage the secondary rotor from the primary rotor in the event of malfunction causing full rotation of the secondary rotor with the primary rotor.

10. A converter for use in a high speed oscillating surgical burring device comprising:
    an output shaft;
    a secondary drive rotor coupled to the output shaft, the secondary drive rotor having a spiral slot defined therethrough and being arranged and configured with a size and mass to minimize its angular momentum;
    a drive pin being disposed through the spiral slot, so that the secondary drive rotor rotationally oscillates as the drive pin longitudinally reciprocates;
    a stationary guide having a linear slot defined therethrough through which the drive pin is disposed to maintain the drive pin in a fixed plane of oscillatory linear motion; and
    a cam follower coupled to the drive pin;
    a primary drive rotor having a cylindrical bore;
    a pair of elliptical intersecting grooves defined in the cylindrical bore, the cam follower engaging the pair of elliptical grooves so that the drive pin is longitudinally reciprocated within the primary drive rotor as the primary drive rotor unidirectionally rotates; and
    an input shaft coupled to the primary drive rotor and to which input shaft a unidirectional rotational force is applied.

* * * * *